United States Patent [19]

Mangold et al.

[11] 3,935,201

[45] Jan. 27, 1976

[54] PRODUCTION OF 2,1,3-BENZOTHIADIAZIN-4-ONE-2,2-DIOXIDES

[75] Inventors: Dietrich Mangold, Neckargemuend; Karl-Heinz Koenig, Frankenthal; Gerhard Hamprecht, Mannheim, all of Germany

[73] Assignee: BASF Aktiengesellschaft, Ludwigshafen, Germany

[22] Filed: Nov. 11, 1974

[21] Appl. No.: 522,630

[30] Foreign Application Priority Data
Nov. 15, 1973 Germany............................ 2357063

[52] U.S. Cl............................................. 260/243 R
[51] Int. Cl.²........................................ C07D 285/16
[58] Field of Search................................ 260/243 R

[56] References Cited
UNITED STATES PATENTS
3,287,362    11/1966    Hurmer et al. ..................... 260/243

*Primary Examiner*—John M. Ford
*Attorney, Agent, or Firm*—Johnston, Keil, Thompson & Shurtleff

[57] ABSTRACT

2,1,3-Benzothiadiazin-4-one-2,2-dioxides are produced by the reaction of esters of anthranilic acid with a sulfamic acid halide in the presence of a solvent and a base at a temperature of from 20° to 100°C. The products are starting materials for the production of dyes and plant protection agents.

7 Claims, No Drawings

PRODUCTION OF 2,1,3-BENZOTHIADIAZIN-4-ONE-2,2-DIOXIDES

The invention relates to a process for the production of 2,1,3-benzothiadiazin-4-one-2,2-dioxides by the reaction of an ester of anthranilic acid with a sulfamyl halide in the presence of a solvent and a base at a temperature of from 20° to 100°C.

German Pat. No. 1,542,836 discloses and illustrates by an Example the cyclization of o-sulfamidobenzoic acid esters into 2,1,3-benzothiadiazin-4-one-2,2-dioxides. Phosphorus oxychloride, thionyl chloride and alkaline solutions are disclosed as cyclizing agents. It is emphasized that the solution of the o-sulfamidobenzoic acid ester in methanol should only be heated for a short time after the alkali has been added and should then immediately be acidified with concentrated hydrochloric acid to pH 1; the reaction mixture has to be cooled rapidly by adding ice prior to the acidification if necessary. The only starting material illustrated by the Example, namely the methyl ester of N-propyl-o-sulfamidobenzoic acid, has to be prepared in a troublesome multistage reaction, involving for example condensation of anthranilic acid with methanol by a conventional method, distillation of the mixture and reaction with an N-acylated sulfamyl chloride.

Cyclization of o-sulfamidobenzoic acid derivatives under the influence of chlorinating and water-eliminating condensing agents is disclosed in German Pat. No. 1,120,456 (column 3, line 43 to column 4, line 2). It is expressly stressed and illustrated in Example 3 that the production of an o-sulfamidobenzoic acid ester serving as starting material and its cyclization into 4-oxo-2,1,3-benzothiadiazine-2,2-dioxide is only successful in one operation when the starting sulfamyl chloride has no substituent on the nitrogen atom. Only end products which are unsubstituted in the 3-position can be prepared in this way. When an o-sulfamidobenzoic acid ester is used as the starting material, ring closure takes place at from 15° to 50°C only in the production of the abovementioned 2,1,3-benzothiadiazin-4-one-2,2-dioxides which are not substituted in the 3-position. It is true that there is mention of the fact that in the case of 3-phenyl and 3-benzyl derivatives it is necessary to use more drastic conditions but no reaction is disclosed. As shown in Examples 4 and 5 and mentioned in the description in column 4, lines 26 to 31 the procedure for the preparation of 3-alkyl derivatives is as follows: an N-formyl-N-alkylsulfamyl chloride is reacted in the absence of bases with an o-aminobenzoic acid ester to form the corresponding N-alkyl-N-formyl-o-sulfamidobenzoic acid ester and the formyl group protecting the nitrogen atom is then eliminated by prolonged heating (five hours) of the reaction mixture, cooling with ice-water and extraction of the mixture with caustic soda solution. The extract is washed with ether and acidified while cooling so that the 3-alkyl-2,1,3-benzothiadiazin-4-one-2,2-dioxide is precipitated. Only Example 4 specifies a yield of end product in the production of 3-alkyl-2,1,3-benzothiadiazin-4-one-2,2-dioxides; this at 27% is inadequate; the process is therefore uneconomical on an industrial scale and is unsatisfactory as regards simplicity and easy control.

An article in J. Amer. Chem. Soc. (1962), volume 84, pages 1994 et seq. describes the reaction of methyl anthranilate and sulfamyl chloride not bearing a substituent on the nitrogen atom in the presence of an organic solvent and of caustic soda solution to form 2,3,1-benzothiadiazin-4-one-2,2-dioxide. The end product is isolated by extraction with caustic soda solution. Cyclization of this starting material under the said conditions gives a multi-component reaction mixture and an end product in an unsatisfactory yield and purity. In order to prepare 3-methyl-2,1,3-benzothiadiazin-4-one-2,2-dioxide it is necessary first to prepare the end product which is not substituted in the 3-position and then to alkylate this with methyl sulfate (page 1994). The process is troublesome and uneconomical.

A process involving cyclization of an o-sulfamidobenzoic acid in the presence of phosgene and a carboxamide bearing two substituents on the nitrogen atom or a tertiary amine at a temperature of not more than 50°C is disclosed in German Laid-Open Specification (DOS) No. 2,105,687. The acid condensing agent necessitates highly corrosion-resistant apparatus and the toxic properties of phosgene make necessary heavy investment for the processing and disposal of offgas. The process is therefore unsatisfactory as regards simplicity, reliability in operation and economy of the plant, control, supervision and ecology.

It is an object of this invention to provide a new process of producing 2,1,3-benzothiadiazin-4-one-2,2-dioxides bearing an aliphatic or cycloaliphatic radical as substituent in the 3-position in a simple and more economical manner and in a better yield and purity.

We have found that a 2,1,3-benzothiadiazin-4-one-2,2-dioxide of the formula (I):

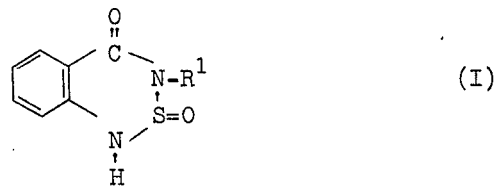

in which $R_1$ is an aliphatic or cycloaliphatic radical is advantageously obtained when an ester of anthranilic acid of the formual (II):

in which $R^2$ is an aliphatic, araliphatic, cycloaliphatic or aromatic radical is reacted with a sulfamyl halide of the formula (III):

in which $R^1$ has the meaning given above and X is a halogen atom in the presence of an inert organic solvent and a basic compound at a temperature of from 20° to 100°C.

When N-isopropylsulfamyl chloride and methyl anthranilate are used, the reaction may be represented by the following equation:

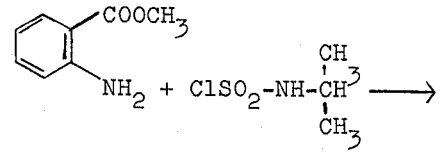

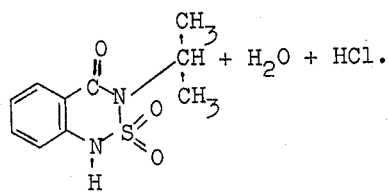 + $H_2O$ + HCl.

As compared with the prior art methods the process according to the invention gives 2,1,3-benzothiadiazin-4-one-2,2-dioxides more simply and more economically in better yields and higher purity. Single-step operation and the use of the starting materials according to the invention offer advantages in industrial operation. Hydrolysis of the end product and formation of byproducts do not take place to any appreciable extent. These advantageous results are surprising having regard to the prior art. In view of the prior art methods it would have been expected that there would be a much lower yield of end product and also secondary reactions such as elimination of the ester alcohol or the alkyl substituents on the nitrogen atom and/or decomposition of the intermediately formed o-sulfamidobenzoic ester and secondary reactions of eliminated groups on the carboxyl group or amino groups of the starting materials (II) and (III), for example by interchange of amido radicals and consequently prevention of cyclization.

The starting materials (II) and (III) may be reacted with one another in stoichiometric amounts or in excess, preferably at a ratio of from 1.1 to 1.5 moles of starting material (III) per mole of starting material (II). Preferred starting material (II) and (III) and accordingly preferred end products (I) are those in whose formulae $R^1$ is alkyl of one to eight and particularly one to four carbon atoms, or cycloalkyl of five to eight carbon atoms, $R^2$ is alkyl of one to eight and particularly one to four carbon atoms, cycloalkyl of five to eight carbon atoms, aralkyl of seven to twelve carbon atoms or phenyl, and X is bromine or preferably chlorine. If desired substances forming the starting materials may be used in the form of the appropriate reaction mixture instead of the starting materials themselves, for example a reaction mixture of isatoic anhydride, methanol and a base may be used instead of methyl anthranilate. The said radicals may bear groups which are inert under the reaction conditions, for example alkyl or alkoxy of one to four carbon atoms, or carbalkoxy of two to four carbon atoms as substituents.

Examples of suitable o-sulfamyl halides for use as starting materials (III) are: N-methylsulfamyl chloride, N-ethylsulfamyl chloride, N-n-propylsulfamyl chloride, N-n-butylsulfamyl chloride, N-isobutylsulfamyl chloride, N-isopropylsulfamyl chloride, N-tert.-butylsulfamyl chloride, N-cyclohexylsulfamyl chloride, N-cyclopentylsulfamyl chloride, N-cyclooctylsulfamyl chloride and the corresponding sulfamyl bromides.

Examples of anthranilic acid esters which are suitable as starting materials (II) are: the methyl, ethyl, n-propyl, n-butyl, isobutyl, isopropyl, tert.-butyl, cyclohexyl, cyclopentyl, cyclooctyl, benzyl, phenyl, tolyl, p-carbomethoxyphenyl and p-ethoxyphenyl esters of anthranilic acid.

The reaction is carried out at a temperature of from 20° to 100°C and preferably from 25° to 85°C, at atmospheric or superatmospheric pressure, continuously or batchwise and in the presence of a solvent. Solvents having a dipole moment of more than 1.2 are preferred. Houben-Weyl, "Methoden der organischen Chemie", volume 3/2, pages 361 et seq. may be referred to for a definition of and method of determining the dipole moment. Examples of suitable solvents thus include halohydrocarbons such as methylene chloride, 1,1-dichloroethane, 1,2-dichloroethane, 1,2-cis-dichloroethylene, n-butyl chloride, 2-butyl chloride, 3-butyl chloride, isobutyl chloride, chlorobenzene, bromobenzene, iodobenzene, o-dichlorobenzene, m-dichlorobenzene, o-dibromobenzene, m-dibromobenzene, o-chlorotoluene, m-chlorotoluene, p-chlorotoluene, 1,2,4-trichlorobenzene, chloro-1,3,5-trimethylbenzene, 1,10-dibromodecane, and 1,4-dibromobutane; ketones such as acetone, acetophenone, cyclopentanone, methyl isobutyl ketone and cyclohexanone; aromatic, aliphatic and cycloaliphatic hydrocarbons such as benzene, toluene, xylene, ligroin, pentane, octane, hexane, heptane, gasoline fractions, for example from 70° to 140°C, cyclohexane and cyclooctane; ethers such as diethyl ether, dipropyl ether, tetrahydrofuran and dioxane; alcohols such as methanol, ethanol, isobutanol, isopropanol, tert.-butanol, ethylhexanol and cyclohexanol; esters such as ethyl acetate, n-butyl acetate, methyl acetate, isobutyl acetate, methyl benzoate and phenyl acetate; nitrohydrocarbons such as nitromethane, nitroethane, nitrobenzene, o-chloronitrobenzene, m-chloronitrobenzene, p-chloronitrobenzene and o-nitrotoluene; nitriles such as acetonitrile, benzonitrile and m-chlorobenzonitrile; tertiary amines such as pyridine, N-dimethylcyclohexylamine, N-dimethylaniline, α-picoline, β-picoline, α-picoline, quinoline, isoquinoline and pyrimidine; or mixtures of the same. The solvent is conveniently present in an amount of from 250 to 400% by weight based on starting material (II).

The starting materials (II) and (III) are reacted in the presence of an organic or inorganic basic compound, conveniently in an amount of from one to three times and particularly from 1.1 to 1.5 times the equivalent weight based on starting material (III). Tertiary amines, alkaline earth metal compounds and particularly alkali metal compounds and appropriate mixtures of the same are the preferred basic compounds. Advantageous alkali metal compounds and alkaline earth metal compounds are the hydroxides, oxides, carbonates and bicarbonates, salts of weak or polybasic acids, and alcoholates of calcium, barium, lithium and particularly of sodium and potassium. The following compounds are examples of suitable basic compounds: potassium hydroxide, potassium carbonate, sodium carbonate, lithium carbonate, sodium bicarbonate, potassium bicarbonate, calcium hydroxide, magnesium oxide, ammonia, barium oxide, calcium carbonate, sodium acetate, sodium propionate, sodium ethylene glycolate, sodium methylate, sodium ethylate, sodium tripropylene glycolate, trimethylamine, triethylamine, quinoline, pyridine, diethylaniline, dimethylaminoethanol, N-ethylpiperidine, N-methylpyrrolidine, diethylamine, aniline, N-dimethylaniline, dimethylcyclohexylamine, ditert.-butylamine, tri-n-butylamine and trimethylbenzylammonium hydroxide. Mixtures of the said basic compounds are also often advantageous.

The reaction may be carried out as follows: A mixture of the starting materials, catalyst and solvent is kept at the reaction temperature for fifteen minutes to two hours. The starting materials are advantageously reacted in two steps in a single bath. A mixture of the starting materials and the solvent and one of the said tertiary amines is kept for from fifteen minutes to two hours at the reaction temperature, advantageously from 40° to 70°C. Then an inorganic basic compound, preferably one of the abovementioned alkali metal compounds, is added and the reaction mixture is kept at the reaction temperature for from fifteen minutes to three hours, preferably at from 40° to 80°C. The abovementioned hydroxides and alcoholates, particularly alkanolates, and mixtures of the same are preferred. When the reaction is over, the benzo-2,1,3-diazin-4-one-2,2-dioxide substituted in the 3-position is present in the reaction mixture in the form of a salt of the base used. It may be isolated particularly easily by taking it up into an aqueous phase. The organic phase which contains solvent and possibly base may be recycled immediately or after purification by distillation. In most cases the end product may be further processed in the form of its salt. It may however be isolated by a conventional method, for example by acidification of the aqueous phase, in the form of 2,1,3-benzothiadiazin-4-one-2,2-dioxide.

The compounds which can be prepared according to the process of the invention are valuable starting materials for the manufacture of dyes and plant protection agents. The said publications are referred to as regards the use of the compounds. Appropriate salts, particularly alkali metal salts, may be prepared from the end products (I) by a conventional method, for example by reaction with a base by the method described in German Patent No. 1,120,456. These salts are plant protection agents and also starting materials for the production of the same.

The following Examples illustrate the invention. The parts specified are parts by weight.

EXAMPLE 1

3.95 parts of isopropylamidosulfonyl chloride is added in a stirred apparatus to a mixture of 8.25 parts of toluene, 3.8 parts of methyl anthranilate and 4.8 parts of tri-n-butylamine at from 20° to 40°C. The mixture is then stirred for another hour at 60°C and then 10 parts of a 30% by weight solution of sodium methylate in methanol is slowly added in portions. The mixture is kept for another hour at from 60° to 80°C so that the methanol added is distilled off. After the whole has been cooled to ambient temperature 12 parts of water is added while stirring and the phases are separated.

The aqueous phase contains the sodium salt of 3-isopropylbenzo-3-thia-1,3-diazin-4-one-2,2-dioxide and this may if desired be further processed in this form.

The aqueous phase is acidified to pH = 1 by adding sulfuric acid. The product is suction filtered and dried. 5.7 parts of 3-isopropylbenzo-2-thia-1,3-diazin-4-one-2,2-dioxide having a melting point of 130° to 132°C is obtained, equivalent to a yield of 93%.

After the organic phase has been dried it is returned to the reaction and distilled. 97% by weight of the amine used is recovered.

EXAMPLE 2

3.18 parts of dimethylcyclohexylamine is used instead of tri-n-butylamine in the procedure described in Example 1. 5.5 parts of 3-isopropylbenzo-2-thia-1,3-diazin-4-one-2,2-dioxide is obtained having a melting point of from 130° to 132°C (91% of theory). 94% by weight of the dimethylcyclohexylamine used is recovered.

EXAMPLE 3

1.9 parts of methyl anthranilate, 1.93 parts of isopropylamidosulfonyl chloride and 1.25 parts of triethylamine are reacted in 5 parts of toluene in the manner described in Example 1. The reaction is completed by adding 1.1 parts of sodium hydroxide in 2.5 parts of methanol and then heating the whole for 1 hour at 60° to 80°C. 2.66 parts of 3-isopropylbenzo-2-thia-1,3-diazinone-(4)-2,2-dioxide (88% of theory) having a melting point of 129° to 132°C.

EXAMPLE 4

2.3 parts of isatoic anhydride, 0.45 part of methanol and 2.6 parts of tri-n-butylamine are reacted for 3 hours at 70°C in a stirred apparatus. Then 7 parts of toluene is added and at 70°C 2.06 parts of isopropylamidosulfonyl chloride is introduced into the solution of the intermediately formed methyl anthranilate. After an hour 4.8 parts (30% by weight) solution of sodium methylate in methanol is introduced and the mixture is stirred for another hour at 60°C. 2.82 parts of 3-isopropylbenzo-2-thia-1,3-diazin-4-one-2,2-dioxide having a melting point of 128° to 133°C (83% of theory) is obtained in the manner described in Example 1.

EXAMPLE 5

As described in Example 1 3 parts of methyl anthranilate, 3.2 parts of isopropylamidosulfonyl chloride and 3.7 parts of tri-n-butylamine in 8.25 parts of toluene are reacted. Then first 3.6 parts of 30% by weight solution of sodium methylate in methanol is introduced and then 1.2 parts of caustic soda. After the mixture has been heated for 1 hour at 60°C it is processed as described in Example 1. 4.2 parts of 3-isopropylbenzo-2-thia-1,3-diazin-4-one-2,2-dioxide having a melting point of 131° to 133°C (88% of theory) is obtained.

We claim:

1. A process for the production of a 2,1,3-benzothiadiazin-4-one-2,2-dioxide of the formula (I):

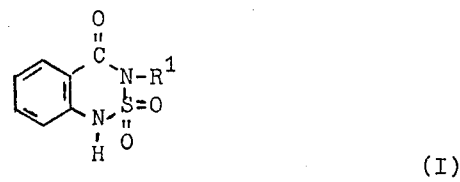

(I)

in which $R^1$ is an alkyl of one to eight carbon atoms, or cycloalkyl of five to eight carbon atoms, wherein the said radicals may bear alkyl or alkoxy of one to four carbon atoms, carbalkoxy of two to four carbon atoms as substituents, which process comprises: reacting an anthranilinic acid ester of the formula (II):

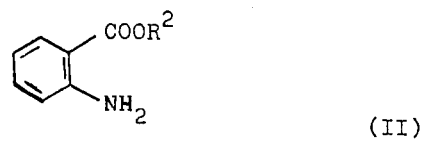

(II)

in which $R^2$ is an alkyl of one to eight carbon atoms, cycloalkyl of five to eight carbon atoms, aralkyl of seven to twelve carbon atoms or phenyl, wherein said radicals may bear alkyl or alkoxy of one to four carbon atoms, or carbalkoxy of two to four carbon atoms as substituents, with a sulfamyl halide of the formula (III):

n which R¹ has the above meaning and X is bromine or chlorine in the presence of an inert organic solvent and a basic compound selected from the group comprising tertiary amines, alkaline earth metal compounds and alkali metal compounds at a temperature of from 20° to 100°C.

2. A process as claimed in claim 1 wherein the reaction is carried out with from 1.1 to 1.5 moles of starting material (II).

3. A process as claimed in claim 1 wherein the reaction is carried out at a temperature of from 25° to 85°C.

4. A process as claimed in claim 1 wherein the reaction is carried out with a solvent having a dipole moment of more than 1.2.

5. A process as claimed in claim 1 wherein the reaction is carried out with a solvent having a dipole moment of more than 1.2 in an amount of from 250 to 400% by weight based on starting material (II).

6. A process as claimed in claim 1 wherein the reaction is carried out in the presence of from one to three times the equivalent weight of said basic compound based on starting material (III).

7. A process as claimed in claim 1 wherein the reaction is carried out in the presence of a hydroxide, oxide, carbonate, bicarbonate, salt of a weak or polybasic acid, an alcoholate of calcium, barium, lithium, sodium or potassium or mixtures thereof.

* * * * *